United States Patent [19]

Speidel

[11] Patent Number: 5,375,605
[45] Date of Patent: Dec. 27, 1994

[54] BLOOD PRESSURE MEASURING DEVICE

[75] Inventor: Blasius Speidel, Jungingen, Germany

[73] Assignee: Speidel & Keller GmbH & Co. KG, Jungingen, Germany

[21] Appl. No.: 969,318

[22] PCT Filed: Jul. 19, 1991

[86] PCT No.: PCT/EP91/01358

§ 371 Date: Feb. 18, 1993

§ 102(e) Date: Feb. 18, 1993

[87] PCT Pub. No.: WO92/03087

PCT Pub. Date: Mar. 5, 1992

[30] Foreign Application Priority Data

Aug. 18, 1990 [DE] Germany ............... 4026242

[51] Int. Cl.⁵ ............................................. A61B 5/021
[52] U.S. Cl. ................................................. 128/677
[58] Field of Search ...................... 128/672, 677–686

[56] References Cited

U.S. PATENT DOCUMENTS

| | | | |
|---|---|---|---|
| 2,560,237 | 7/1951 | Miller | 128/677 |
| 3,613,667 | 10/1977 | Beck | 128/677 |
| 3,901,217 | 8/1975 | Clark | 128/677 |
| 4,010,739 | 3/1977 | Leach | 128/677 |
| 4,108,310 | 3/1976 | Aldridge et al. | 206/570 |
| 4,222,390 | 9/1980 | Berliner et al. | 128/677 |

FOREIGN PATENT DOCUMENTS

| | | |
|---|---|---|
| 0008351 | 7/1979 | European Pat. Off. |
| 0397392 | 11/1990 | European Pat. Off. |
| 1535709 | 6/1967 | France |
| 2109035 | 5/1972 | France |
| 2275182 | 6/1975 | France |
| 2053782 | 11/1971 | Germany |
| 2707952 | 9/1977 | Germany |
| 2740182 | 3/1979 | Germany |
| 2814766 | 4/1979 | Germany |
| 1594230 | 7/1981 | Germany |
| 3323624 | 1/1985 | Germany |
| 8015739 | 6/1989 | Germany |
| 2106249 | 4/1983 | United Kingdom |

*Primary Examiner*—Angela D. Sykes
*Attorney, Agent, or Firm*—Foley & Lardner

[57] ABSTRACT

The blood pressure measuring device (10) has a bowl-shaped casing (11) in which is arranged a pressure measuring system with a measuring scale (13) and indicator. The casing (11) is closed at its upper edge by a transparent cover plate (25). This primary casing (11) is surrounded at a given distance on the outside by a protective housing (15), whereby the base (18) of the protective housing (15) is combined in one piece with the base (16) of the primary casing (11). The compressed air line is connected either through a hole (22) in the base (16) of the casing (11) or through the casing walls. In the latter case, there is a material bridge in the space between the wall of the primary casing (11) and of the protective housing (15).

7 Claims, 2 Drawing Sheets

BLOOD PRESSURE MEASURING DEVICE

BACKGROUND OF THE INVENTION

In most of the known sphygmomanometers the manometer is contained in a usually cup-shaped case and is mounted therein on one of the parts of the case. This case also contains the dial through which the meter shaft passes. Above the dial the pointer is mounted on the meter shaft. The dial, and the pointer are covered by a crystal which is either inserted directly on the upper margin of the case or is inserted in a separate bezel which in turn is joined to the margin of the case (EP-A-0 008 351 A2). In both cases the disk seals the interior of the case, with the parts contained therein, from the exterior.

If such a sphygmomanometer falls onto a hard surface there is the danger that the case may be damaged, especially that it may be distorted. In the area of the bottom, and of the transition from the bottom to the circumferential wall, the case has of its nature a comparatively great stability of shape, so that in this area the distortions caused by dropping generally remain comparatively slight. It is different when the case strikes in the area of its top margin where the dial and the crystal become damaged. The dial may be bent or may bulge. Such deformation of the dial can be so great that the pointer can no longer move across the dial.

If the case becomes deformed the dial may also snap out of its mounting. The same applies to the crystal. In the event of a particularly hard shock the spiral return spring of the manometer mechanism may become damaged, when for example one or more of its coils loop over one another and become entangled. In the case of all such damage or even destruction of individual parts, the entire sphygmomanometer becomes useless.

SUMMARY OF THE INVENTION

It is the object of the invention to construct a sphygmomanometer such that the damage or destruction caused by dropping it will at least be reduced if not entirely prevented.

Since the primary case is surrounded by a protective case, if the sphygmomanometer falls on a hard surface the circumferential wall of the interior primary case might not be struck, so it cannot be deformed. Consequently the danger that the meter and its parts contained in the primary case might be damaged is almost entirely avoided. In particular, the primary case is prevented from being dented in the area of its upper margin where the dial and crystal are fastened. Therefore these parts are virtually entirely protected against damage. Since the bottom of the protective case is integral, at least at approximately the same level, with the outside of the bottom of the circumferential wall of the primary case, the strength of the entire case is considerably increased in this area. For this reason alone, deformation of the primary case in this area is entirely prevented, and the danger of deformation even of the protective case is greatly diminished.

If the sphygmomanometer is designed in accordance with claim 2, it becomes easier to attach the manometer mechanism to the other parts of the sphygmomanometer which are disposed on the outside of the bottom of the case. In an alternative configuration of the sphygmomanometer according to claim 3, the same will be true for attachment in the area of the side wall of the entire case, if the rest of the parts of the sphygmomanometer are attached there.

In an embodiment of the sphygmomanometer according to claim 4, the guard ring disposed on the upper margin of the protective case closes off the gap between the circumferential wall of the primary case and the circumferential wall of the protective case. This at least greatly reduces, if not entirely prevents, the penetration of dust and dirt into this gap. Also, since the guard ring extends inward at least to the edge of the primary case or extends slightly past it, the upper edge of the primary case with the crystal placed in it and the dial set below it are also protected at the face of the sphygmomanometer.

In a further development of the sphygmomanometer according to claim 5, the danger of damage to the guard ring is reduced since its beveled outside face eliminates the sharp edge which would be more exposed to damage by striking against a hard surface. This shaping of the guard ring increases the impact area and thereby reduces the stress per unit area at the point of impact. Furthermore, it makes it easier for the case to roll on the surface, which also contributes to the reduction of peak stresses.

By a configuration of the sphygmomanometer according to claim 6, the assembly of the guard ring is simplified and facilitated.

In an embodiment of the sphygmomanometer according to claim 7, the elastic ring between the guard ring and the protective case absorbs part of the impact energy if the case should strike with its guard ring against a hard surface. In this manner too, the danger of damage to the parts of the sphygmomanometer is considerably reduced.

BRIEF DESCRIPTION OF THE DRAWINGS

The invention will now be explained with the aid of two embodiments represented in the drawing, wherein.

Figure 1:
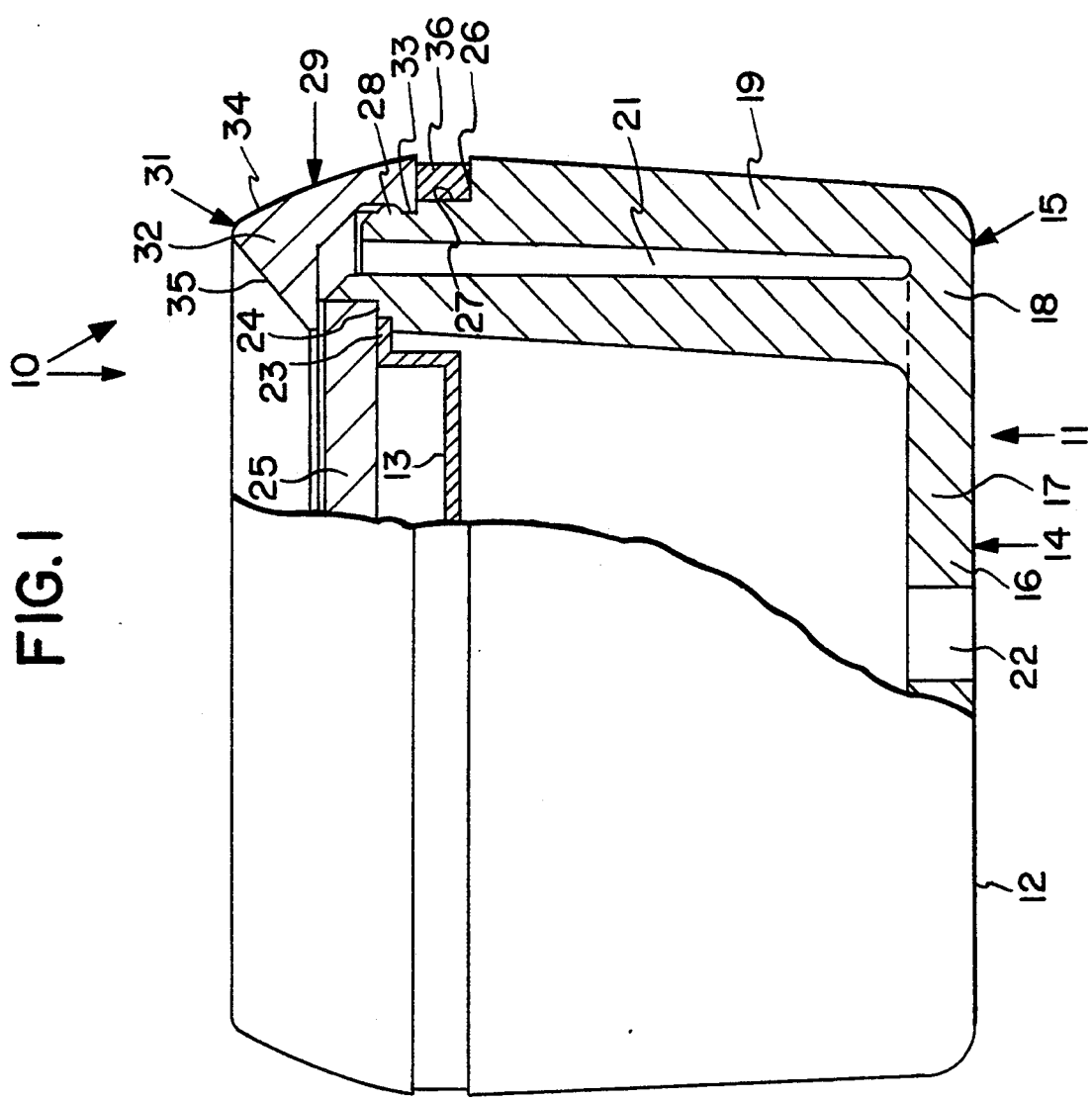
FIG. 1 is a partially cut-away view of a case of the sphygmomanometer in which most of the parts of the manometer mechanism are not represented.

The sphygmomanometer 10 seen in section in FIG. 1 has an at least approximately cup-shaped case 11. In its interior 12 the manometer mechanism of conventional design is housed, of which only the dial 13 is represented in FIG. 1.

The case 11 is a kind of double case with an interior or primary case, referred to hereinafter as primary case 14, and with an external or secondary case which, due to its special function, will be referred to hereinafter as protective case 15. The case 11 with its two parts 14 and 15 is made in one piece of molded plastic.

The primary case 14 is cup-shaped and has a bottom 16 and a circumferential wall 17. The protective case 15 has at least approximately the same shape and also has a bottom 18 and a circumferential wall 19. The bottom 18 of the protective case 15 joins at the same level the bottom 16 of the primary case, at the outside of the circumferential wall 17 thereof. Thus the bottom 18 is reduced to an annular area whose radial width is only as great as the radial width of the gap 21 between the circumferential wall 17 of the primary case and the circumferential wall 19 of the protective case 15.

The primary case 14 has in the center of the circle of its bottom 16 a cylindrical bore 22 through which the compressed air carrying parts of the sphygmomanometer 10 communicate with the manometer mechanism contained in the interior chamber 12.

At the upper margin of the wall 17 of the primary case 14, two ledges 23 and 24 of graded diameter are present. On the lower inner ledge 23 lies the margin of the dial 13, and the margin of a crystal 25 lies on the upper ledge. The circumferential surface of the crystal 25 and the section of the inside of the circumferential wall 17 adjoining the ledge 24 are configured as frusto-conical surfaces with a very small cone angle. This results in a kind of snap fastening which holds the crystal 25 on the top margin of the primary case 14 when it has been inserted therein. The crystal 25 then also holds the dial 13 in place.

On the circumferential wall 19 of the protective case, a rabbet 26 with a flat, circular surface is present. It is defined on the inside by a cylindrical surface 27. In the adjoining longitudinal section of the circumferential wall 19, whose outside has at least approximately the shape of a cylinder, there is formed an annular bead 28 protruding radially outward. This bead, as a projection of the wall, forms the one part of a snap fastening 29 by which a guard ring 31 is held, which is placed downwardly onto the circumferential wall of the protective case 15. On the inside of a circumferential wall 32 of the guard ring 31 there is formed an inwardly projecting annular bead 33 which catches on the annular bead 28 on the circumferential wall 19 and acts as the catch of the snap fastening 29.

The guard ring 31 has a gable-like cross section with sides of unequal width. The outer side 34 of the guard ring 31 has a curved profile, and the inner side 35 of the guard ring 31 has a straight profile.

As it can be seen in FIG. 1, the guard ring 31 reaches inwardly from the outside of the circumferential wall 19 of the protective case 15 to beyond the circumferential wall 17 of the primary case 14, so that it slightly overlaps the crystal 25 at the margin of the wall 17. The margin of the guard ring 31 is not directly in contact with the crystal 25 but is at a short distance away from it for safety, so that if the guard ring 31 undergoes an elastic deformation it will not immediately impact the crystal 25.

To enable the guard ring 31 to serve its purpose in an optimum manner, it is best made of a plastic having greater resistance to impact and fracture than the material of the case 11.

The snap fastening 29 is so configured that it can still shift slightly in the axial direction against the protective case 15 when it is snapped onto the margin of the latter. Between the rabbet 26 of the protective case 15 and the downwardly directed face of the circumferential wall 32 of the guard ring, an intermediate ring 36 which is resilient at least in the axial direction is inserted. This ring damps shocks which under certain circumstances strike downwardly against the guard ring 31.

Instead of an intermediate ring 16 made of an elastomer, a ring made of a less elastic or even hard material can be used, which on account of its material—a metal for example—or due to its special color provides a contrast with the color of the protective case 15 and/or with the guard ring 31.

Figure 2:
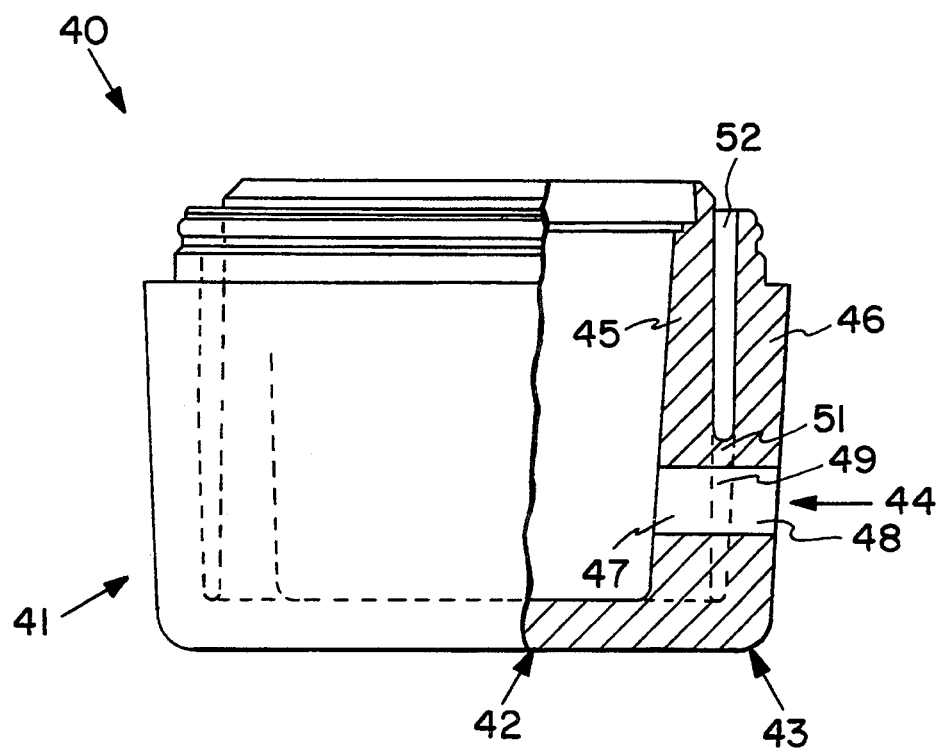
FIG. 2 is a partially cut-away view of the case of a second embodiment of the sphygmomanometer.
Figure 3:
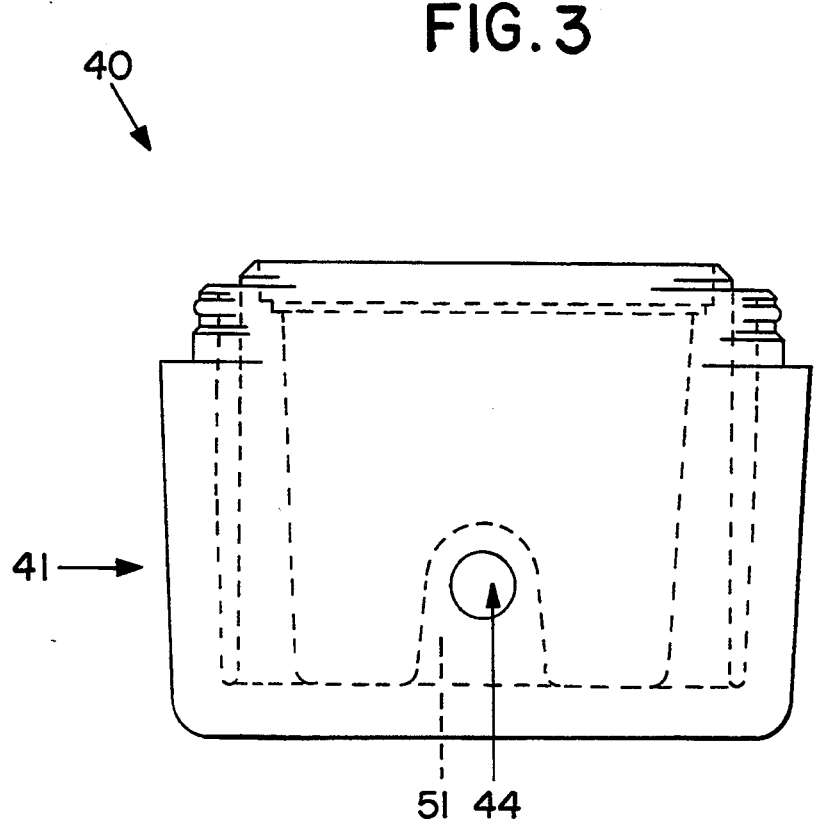
FIG. 3 is a view of the case according to FIG. 2 represented as rotated 90° on its axis.

In the sphygmomanometer shown partially in section in FIGS. 2 and 3, only the case 41 is different in some ways from case 11. The other parts of the sphygmomanometer 40, which are not all shown, are to be considered as the same or at least similar to the corresponding parts of sphygmomanometer 10.

The outside and inside dimensions of case 41 are virtually the same as those of case 11. It likewise has two parts, namely the primary case 42 and the protective case 43.

The manometer mechanism contained in the interior of case 41 is not connected by a bore in the bottom of the case to the other parts of the sphygmomanometer 40 which carry compressed air, but is connected by a connecting line 44 which is disposed in the area of the circumferential wall 45 of the primary case 42 and the circumferential wall 46 of the protective case 43. This connecting line 44 is formed by a through-bore 47 in the circumferential wall 45, by a through-bore 48 in the circumferential wall 46, and by a through-bore 49 in a bridge 51. In the area of the connecting line 47, this bridge 51 fills up the gap 52 running all the way around between the circumferential wall 45 of the primary case 42 and the circumferential wall 46 of the protective case 43, and thus seals off the connecting line 44.

I claim:

1. A sphygmomanometer comprising:

a primary case having a bottom wall and a circumferential wall extending from said bottom wall to define an interior space therebetween;

a manometer having a shaft and being fastened to said primary case within said interior space;

a dial disposed on an upper margin of the primary case, said shaft passing through said dial;

a pointer fixed to said shaft above a surface of said dial;

a crystal removably joined to said upper margin;

a protective case having a bottom wall and a circumferential wall, said circumferential wall of said protective case extending from said bottom wall of said protective case and surrounding said circumferential wall of said primary case to define a gap therebetween, said bottom wall of said protective case integrally joined to an outside surface of said circumferential wall of said primary case at approximately a same level as said bottom wall of said primary case such that said primary and a protective cases are a single piece construction.

2. A sphygmomanometer as recited in claim 1, further comprising a cuff and a compressed air line connecting said cuff to said manometer, and wherein said bottom wall of said primary case has a through-bore therein through which said compressed air line passes.

3. A sphygmomanometer as recited in claim 1, further comprising a bridge disposed in said gap, a cuff and a compressed air line connecting said cuff to said manometer, and wherein said circumferential walls of said primary and protective cases respectively include first and second through-bores which are aligned with each other, said compressed air line passes through said first and second through-bores, and said bridge seals and encompasses a section of said gap which is located between said first and second through-bores.

4. A sphygmomanometer as recited in claim 1, further comprising a guard ring disposed at a top margin of said circumferential wall of said protective case, said guard ring extending from an outside surface of said circumferential wall of said protective case to at least said upper margin of said primary case but not beyond a scale portion of said dial, and said guard ring being made from a material which has a greater impact and fracture resistance than a material from which the protective case is made.

5. A sphygmomanometer as recited in claim 4, wherein an outside surface of said guard ring is tapered away from said top margin and is configured as at least one of a truncated cone mantle surface and a surface of a section of a sphere.

6. A sphygmomanometer as recited in claim 4, further comprising a snap fastener, said snap fastener including a partially circumferential projection and a partially circumferential indentation into which said circumferential projection is removably disposed to secure said guard ring to said protective case.

7. A sphygmomanometer as recited in claim 6, further comprising an intermediate ring which is elastically flexible at least in an axial direction of said shaft, said intermediate ring disposed between an annular surface of said guard ring and an annular surface of said protective case such that said snap fastener is flexible in said axial direction or moveable in the axial direction.

* * * * *